United States Patent [19]
Smith

[11] Patent Number: 5,869,158
[45] Date of Patent: Feb. 9, 1999

[54] SAFETY SAMPLER

[75] Inventor: Michael W. Smith, Fairburn, Ga.

[73] Assignee: Porex Technologies Corp., Fairburn, Ga.

[21] Appl. No.: 990,098

[22] Filed: Dec. 14, 1992

[51] Int. Cl.⁶ .................................... B29D 22/00
[52] U.S. Cl. ............... 428/36.92; 428/36.9; 604/272; 604/239; 604/240; 604/905; 604/275; 604/264; 606/181; 606/167
[58] Field of Search ............................ 604/272, 239, 604/240, 905, 275, 264; 606/181, 167; 428/36.9, 36.92

[56] References Cited

U.S. PATENT DOCUMENTS

| D. 310,569 | 9/1990 | Broden | D24/51 |
|---|---|---|---|
| 2,514,576 | 7/1950 | Hein et al. | 128/232 |
| 3,206,073 | 9/1965 | Scislowicz | 222/80 |
| 3,234,944 | 2/1966 | Stevens et al. | 604/240 |
| 3,886,928 | 6/1975 | Sarstedt | 128/2 F |
| 3,941,167 | 3/1976 | Haury-Wirtz et al. | 141/1 R |
| 4,057,060 | 11/1977 | Roth | 128/232 |
| 4,747,839 | 5/1988 | Tarello et al. | 604/240 |
| 4,808,381 | 2/1989 | McGregor et al. | 422/100 |
| 4,909,800 | 3/1990 | Gross | 604/272 |

FOREIGN PATENT DOCUMENTS

| 2164363 | 7/1973 | Germany . |
| 3323867 | 1/1985 | Germany . |

*Primary Examiner*—Jose G. Dees
*Assistant Examiner*—Michael A. Williamson
*Attorney, Agent, or Firm*—Lane, Aitken & McCann

[57] ABSTRACT

A fluid transfer device has a resilient reservoir connected to a rigid hollow punch made of synthetic resin. The punch is precisely sized to enable manual penetration of rubber stoppers found on standard evacuated tubes which are commonly used for blood sampling. The diameter of the punch also allows for transfer of the fluid from the sample tube to the device in a reasonable amount of time. A method of transferring blood or blood products from the sample tube to testing apparatus involves using the device to penetrate a rubber cap on an evacuated tube and then transfer the blood to the device. The blood can then be transferred to a testing apparatus without exposure to the atmosphere.

7 Claims, 1 Drawing Sheet

SAFETY SAMPLER

This invention relates to the transfer of fluids and more particularly to the transfer of blood or blood sera from evacuated tubes to testing apparatus.

BACKGROUND OF THE INVENTION

Physicians require blood tests for a variety of reasons and current technology allows a physician to learn much about a patient's condition by testing blood alone. One standard sampling procedure for blood involves the use of a pre-evacuated test tube and a cannula with two penetrating ends. In order to obtain a blood sample, one end of the cannula is inserted into the donor's vein and the opposite end of the cannula is inserted through a rubber cap which makes an air tight seal on the end of an evacuated tube. The pre-evacuated tubes are sealed with a cap or plug which makes an air tight seal and maintains negative pressure in the tube. One such commercially available tube is manufactured by Becton Dickenson, of Rutherford, N.J. and sold under the trademark VACUTAINER. Some tubes are sold with gels or other filter means which are designed to be inserted in a centrifuge to separate various components in blood. The tubes have a round bottom and are made or either glass or plastic with a silicone rubber stopper. The stopper is typically constructed of isobutylene-isoprene rubber or chlorinated isobutylene-isoprene rubber. The stoppers are inserted in the tubes very tightly to prevent spillage and the loss of pressure during shipment. Negative pressure maintained in the tube facilitates the transfer of blood from the donor to the test tube. Intravenous blood pressure of the patient also provides assistance to flow blood from the vein to the test tube and, in fact, intravenous blood pressure can create positive pressure in the sampling tube after the sampling procedure is completed. After the sample is retrieved, the needle is withdrawn from the rubber stopper and is suitably disposed. The rubber stopper collapses and re-seals itself to maintain an air-tight condition. The sampling tube serves as a convenient and safe storage receptacle for the sample which can be sent to laboratories in remote locations from the sampling location for analysis.

After the sampling procedure, a barrage of tests may be performed on the blood sample each of which require a portion of the fluid from the sample. In hematology, whole blood samples are used. A number of other clinical chemical blood analyses require the separation of various components from whole blood before testing because the components may interfere with the administration of the analyses. For example, many analyses require the separation of cellular components and the fibrin from the blood before testing. Separation procedures, which can involve filtration or centrifugation and combinations thereof, are often performed in the evacuated sample tube. The primary difference between serum and plasma is their content of fibrinogen which is in large part removed by the clotting process. Fibrinogen, which is present in blood plasma, is converted to fibrin during clotting of blood. Regardless of the test procedure used, when whole blood, blood serum or blood plasma is tested, a portion of the liquid must be removed from the evacuated sample tube and transferred to the testing apparatus. Consequently, a number of methods and apparatus for this procedure have been developed which attempt to balance competing considerations of safety, convenience, and expense. The transfer should be able to be effected quickly with low cost while maintaining a safe environment for the blood technicians. Blood may contain biologically hazardous components which can expose laboratory technicians to the risk of contracting contagious disease. Accordingly, the potential for exposure to the blood should be minimized. Furthermore, it is important to ensure the blood or fluid is not contaminated during the transfer procedure which could lead to inaccurate testing results.

Present sampling procedures employ a number of different methods to effect this type of transfer however each transfer method has a number of disadvantages and limitations. For example, one current procedure for the sampling of blood components from evacuated tubes involves the removal of the cap or plug from the sample tube and then either pouring the sample from the tube or using a transfer device such as a pipette. The removal of the cap however presents an unnecessary risk of exposure. The blood could be spilled or released into the air by an aerosol effect. Due to engineering constraints, removal of the cap places high stress on a test tube which could fracture the tube thereby presenting another avenue of exposure. The cap forms a tight seal with the tube to maintain an air tight condition and, accordingly, the manual manipulation of the cap is difficult. More importantly, the removal of the cap can cause a dangerous aerosol effect, especially when the pressure within the sample tube is different from the air pressure in the environment. When the tube is under positive pressure the aerosol effect is exacerbated because air rushing out of the tube can propel small drops into the air. When the cap is removed from the tube, it is often placed upon the technician's working surface which can then contaminate the working surface and present a further risk to the technician. Contamination of the working surface also presents the risk of contamination of the remainder of the sample under analysis from blood which has escaped from previously tested samples and is present on the technicians' working surface.

After removal of the cap, the blood must be transferred by suitable means to the testing apparatus. Preferably the transfer device should be disposable to avoid the problems and expense associated with cleaning the device after use. Furthermore the transfer device should be easy to manipulate, minimize exposure of laboratory technicians and be capable of quick and easy operation. Pipettes, which can be constructed of glass or plastic, are routinely used to obtain blood or serum samples either directly from evacuated tubes or from open storage receptacles. Pipettes however have a number of disadvantages for the instant application. Although pipettes are effective at transferring small precise volumes of fluid to precise locations, pipettes are also not well suited to transfer larger amounts of liquid from a sample test tube because they have no fluid reservoir. Use of pipettes would take an unreasonable amount of time to transfer larger volumes of fluid from a sample tube to another location. Pipettes must be provided with a means for suction to draw the liquid into the narrow tube. One common device is a resilient bulb which is constructed of rubber and intended to be reused. These bulbs are relatively expensive and somewhat difficult to manipulate because they must be changed from each pipette. Furthermore the bulbs require cleaning in the event blood is drawn into the structure.

There are disposable pipettes commercially available which have an integral resilient bulb designed to draw fluid into the pipette. The bulb can serve as a fluid reservoir, but the device is not generally designed to quickly transfer larger amounts of fluid.

A further drawback associated with the use of pipettes relates to the risk of contamination. Since sampling requires immersion of the end of the pipette in blood, the outer surfaces of the pipette are covered with blood. Although the pipettes are disposable, this exposed surface presents the possibility of the blood dripping off on to the technician or the working surfaces.

Recapping the tubes also presents yet another opportunity for spillage and exposure from contact with the stopper which is often contaminated with blood.

One method to obtain a blood sample while avoiding the removal of the cap is to penetrate the cap with the transfer device. Commercially available pipettes are not strong and durable enough to penetrate the standard rubber cap on an evacuated tube or designed for such penetration. For example, the diameter of disposable transfer pipettes which were previously described and are currently on the market is typically 0.130 inches with a 0.090 inch diameter fluid passageway. Pipettes with such dimensions will not puncture the rubber cap on an evacuated tube without considerable effort. Even if such pipettes were strong enough to puncture a rubber cap without breaking, they are not well designed for this purpose because there is no flange structure to adequately hold the pipette and allow the application of sufficient force to puncture a rubber cap or plug. Furthermore the ends of pipettes are not sharpened to a point which would help enable the pipette to penetrate a cap.

Conventional micro pipette assemblies which include a holder, a pipette and an overflow chamber are likewise not well suited for this application. There are a number of ancillary devices sold in association with pipettes for the specific purpose of puncturing diaphragms on reservoirs containing diluents and other types of medicants, however these devices are not designed to puncture the relatively thick caps employed with pre-evacuated tubes.

One device which avoids removal of the rubber cap in blood sampling recognized the problems associated with current procedure and disclosed using a punch to puncture the stopper on such standard evacuated tubes and draw the sample through the hole made in the stopper made by the punch. It is apparent that the developer considered the problems with designing a punch which would allow a technician to exert sufficient amount of force on the punch to penetrate the rubber cap because the device included a cowling or shroud for alignment purposes and contemplated the use of a mechanical press mechanism in order to puncture the rubber stopper. After insertion into the rubber stopper, the punch is apparently intended to remain in the sample tube. The size of the punch disclosed apparently results in an opening too large to be resealed by the collapse of the stopper. Inserted within the punch is a pipette which has a resilient reservoir for sampling the liquid in the sample test tube. One embodiment does not provide an air tight seal between the interior walls of the punch and the exterior walls of the pipette and as such the system can only be used in an upright position. This arrangement is not desirable because the remaining sample is exposed to the air and presents the problems associated with spillage or the opening must be sealed with a second cap. The central passage of the punch disclosed in the prior art must be able to receive a typical transfer pipette which has an outer diameter of approximately 0.130 inches. A punch made this size would be too large to manually penetrate a typical rubber stopper without considerable effort. Punches which have large diameters exert greater stress on the sample tube which increases the risk of accidental fracture of the tube and the potential for coring of the stopper.

Some of these limitations were recognized and another embodiment was proposed with a second cap designed to fit in the hole formed by the punch. Within the second cap is a diaphragm comprised of polyurethane foam. The diaphragm has a vertical cut specifically designed to be able to be penetrated by a sampling pipette.

Metal needles or punches are commonly used to penetrate rubber stoppers such as those found on bottles which contain medicine or drugs and from evacuated tubes; however, the use of metal is undesirable because of the risk of accidental puncture injury. Currently the use and disposal of "sharps" is subject to a number of regulations because of the risk of accidental contamination and needle sticks. Furthermore, smaller needles would take an unreasonable amount of time and would not provide an expedient means for the transfer because of the small diameter of the passageway. Metal needles or punches also present problems associated with the attachment of the needle to the receptacle. Accordingly, the use of metal components is best avoided.

BRIEF DESCRIPTION OF THE INVENTION

The present invention provides an inexpensive device designed to transfer blood or blood serum which can penetrate the rubber stoppers on commercially available vacuum tubes. The fluid transfer device according to the invention has a translucent resilient receptacle constructed from a soft plastic polymer such as polyurethane or polyethylene connected with a hard plastic punch which is sufficiently small to penetrate a rubber stopper with relative ease yet sufficiently large to define a cannula suitable for blood sample transfer including whole blood samples and provide sufficient strength to avoid failure during penetration.

DETAILED DESCRIPTION OF THE INVENTION

Figure 1:
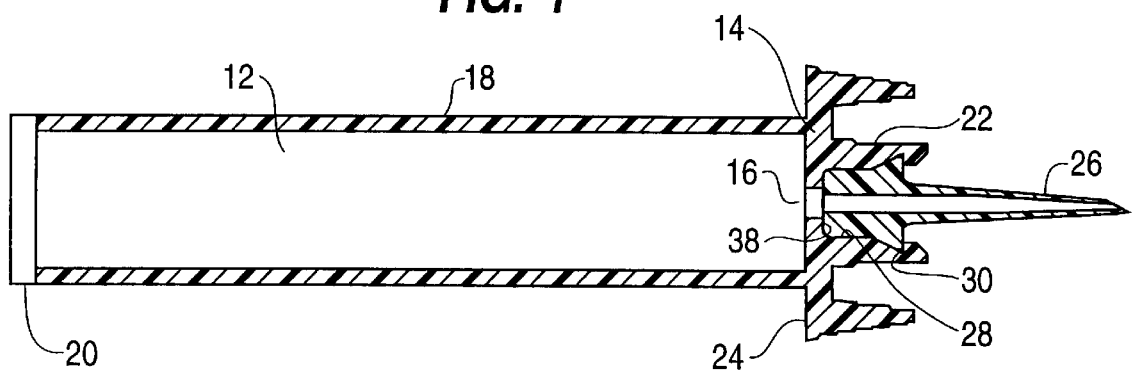
FIG. 1 is an axial section of the fluid transfer device according to the invention.
Figure 2:
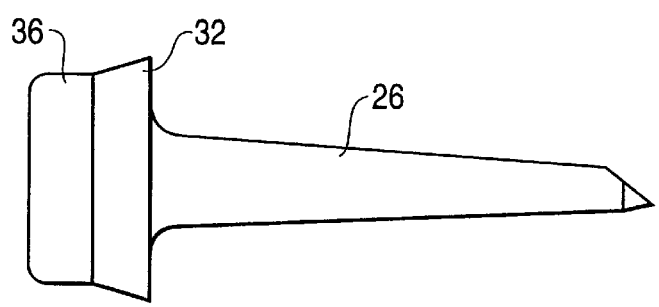
FIG. 2 is a plan view of the punch according to the invention.

Referring now to FIG. 1., elongated reservoir 12 is defined by a cylindrical endwall 14 having a central opening 16, and sidewall 18 which tapers to a flat thermoplastic seal 20. Axially projecting from endwall 14 and concentric with opening 16 is a cylindrical sleeve 22. Extending radially from the end wall is an integral flange 24 in the form of an annular ring. The receptacle, flange and sleeve are preferably formed of polyethylene or similar resilient plastic such as polyvinylchloride. Furthermore the receptacle is preferably transparent or translucent to enable the blood technician to see the fluid as it is drawn into the fluid transfer device. The cylindrical sleeve receives a punch 26 made of a hard synthetic resin such as polycarbonate. Other materials that could be used include high impact styrene, polyphenylene sulfide, polyethylene terephthalate, polybutylene terephthalate, polyphenylene oxide, acetal, nylon, acrylonitrile butadiene styrene, styrene-butadiene, polyethersulfone, polyesters, phenolics and polyamide. The word "plastic" used herein means synthetic resin. On the inner surface 28 of cylindrical sleeve 22 is an annular groove 30 designed to receive a shoulder 32 of punch 26. The sleeve 22 has a constant diameter which is slightly smaller than the diameter of the punch at the shoulder 32. Since the plastic is resilient, the punch can be forced into the sleeve and snap-fit into position. The base 36 of punch 26 is seated on an outer face 38 of the endwall. The shoulder is engaged by the groove to retain the punch securely in the sleeve. The base 36 of the punch fits tightly within the sleeve and is contiguous with the inner surface 28 of the sleeve and the outer face 38 of the endwall.

Figure 3:
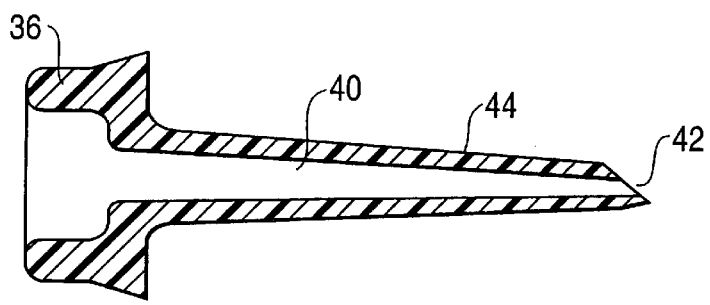
FIG. 3 is an axial section of the punch according to the invention.

As best shown in FIG. 3, the punch 26 according to the invention has a central passage 40 with a diameter of approximately 0.015 inches at the opening 42, its smallest point. An opening substantially smaller than 0.015 inches would decrease the ability of the punch to transfer blood samples from an evacuated tube to the testing apparatus at a reasonable rate. Openings substantially larger than this optimal size would correspondingly impair the punch's ability to penetrate a stopper and would also present the problem of coring. Coring refers to the circumstance where the circular walls of a punch severs and removes a section of rubber from the stopper which results in an opening that will not reseal. In such instances, after the punch is withdrawn from the cap the rubber does not sufficiently collapse to seal the opening and the sample tube is no longer air tight and may otherwise leak. The rubber section cut from the stopper can also interfere with the flow of liquid into the fluid transfer device.

The walls 44 defining the central passage have a minimum thickness of 0.015 inches near the opening and gradually become thicker as the punch tapers to the base 36 of the punch. This dimension has been experimentally found to be the smallest thickness which would retain the strength necessary for hard plastic as mentioned to penetrate the stoppers on standard evacuated tubes. Accordingly, the minimum diameter of the punch at its distal end is approximately 0.045 inches. The maximum diameter of the punch has been found to be approximately 0.090 inches. Metals such as stainless steel could conceivably be used to construct a punch having thinner walls, however the use of metal is undesirable in lab applications because of the increased potential for accidental puncture injuries. Walls constructed of plastics substantially smaller than 0.015 inches increase the chance of failure to unacceptable levels. In other words, if the walls were made much smaller than that taught by the invention, the punch may break or bend under the pressure required to penetrate the stopper.

From its distal end, the punch increases its diameter from 0.045 inches to 0.090 inches where it meets the base 36. Thus the punch has a small diameter for ease of initial penetration and extends to a larger diameter at the base to stabilize the punch and minimize the tendency to bend. The central passage 40 in the punch extends axially from the opening 42 and gradually increases in diameter until the base section where the opening significantly increases to approximately 0.132 inches. The passage extends through the base section at a constant diameter and exits. When in position within the sleeve, the central passage 40 is aligned with the central opening 16 of endwall 14 of the reservoir. The tip of the punch is molded at an oblique angle to further facilitate entry of the punch into the rubber stopper. Although polycarbonate is the preferred embodiment for the punch, other engineered resins would also have sufficient hardness and strength to operate in the punch according to the invention. The punch must be able to transfer a volume of blood in a reasonable amount of time while at the same time be small enough to easily penetrate the rubber caps supplied with standard evacuated tubes. The punch according to the invention can penetrate stoppers made from thermoset rubbers, thermoset silicone elastomers, thermoplastic polyurethanes, polyester thermoplastic elastomers, olefinic thermoplastic elastomers, polyurethane thermoplastic elastomers, styrenic thermoplastic elastomers and ethylene vinyl acetate. Larger punches are difficult to manually force through the rubber stoppers and present the problem of coring. The punch element of the fluid transfer device is constructed to precise dimensions which allow the punch to be able to both puncture the stopper and serve as a conduit from a standard pre-evacuated tube to the fluid reservoir of the testing apparatus. To minimize the force required to pierce the stopper the punch is made as small as possible, however the punch could not be made so small that the passage of fluid into the device takes an unreasonable amount of time. Because the primary purpose of the invention is directed towards sampling and transferring blood from pre-evacuated tubes, it is necessary to design and engineer the size of the punch so that it will be suitably compatible with the viscosity of blood. Furthermore the punch must be large enough to allow blood cells to pass through the punch without damage and be able to transfer a fluid with the same viscosity as blood with relative ease.

In operation, a blood technician perpendicularly aligns the punch element of the transfer device above the rubber stopper on a standard tube used for blood collection or storage. The technician holds the device with the thumb and forefinger against the resilient walls 18 of the reservoir and the flange 24 and applies downward pressure. If the sample test tube is suspected to have a positive air pressure gradient, the technician can first apply a slight pressure to the resilient walls of the receptacle before the seal formed by the stopper is penetrated. This precaution will allow the technician to safely equalize the pressure differential between the two receptacles and prevent the formation of potentially dangerous aerosols.

Since the punch forms a tight seal between the rubber stopper and the outer wall of the punch, the test tube can be inverted without risk of spilling the contents. The application of pressure on the resilient reservoir will create a pressure differential between the sample tube and the transfer device. Release of the pressure allows the reservoir to expand and draw liquid from the sample tube through the punch and into the reservoir. This procedure can be repeated until the reservoir is full. After the desired volume is transferred to the reservoir, the punch is removed from the rubber stopper and the stopper reseals itself. The rubber stopper also wipes any fluid from the outer wall of the punch thereby minimizing exposure to the technicians. Fluid is retained in the sampler even when the device is inverted by capillary action. When the device is in the desired position, pressure can be applied to the resilient walls of the reservoir to discharge the fluid into the testing apparatus. Accordingly the invention avoids exposure of the blood to the atmosphere while at the same time minimizing the potential for exposure to the technicians. Furthermore, because the device is made entirely of plastic, no sharps are employed in the process which make the procedure safer. The use of a plastic punch also avoids the necessity to follow all of the regulations governing the use and disposal of "sharps".

I claim:

1. A fluid transfer device comprising a receptacle formed by resilient sides defining a reservoir and an opening, a punch made of synthetic resin with a central passage, and connecting means to retain said punch on said receptacle and align said central passage over said opening, said punch having walls defining said central passage, said punch having a distal end with a minimum diameter of approximately 0.045 inches, a maximum diameter of approximately 0.090 inches and said central passage having a minimum diameter of approximately 0.015 inches and said wall having a minimum thickness of approximately 0.015 inches.

2. The device according to claim 1 where said punch is comprised of synthetic resin comprised of one of the following materials: polycarbonate, high impact styrene, polyphenylene sulfide, polyethylene terephthalate, polybutylene terephthalate, polyphenylene oxide, acetal, nylon, acrylonitrile butadiene styrene, styrene-butadiene, polyethersulfone, polyester, phenolic or polyamide.

3. The device according to claim 1, wherein said punch is made of a synthetic resin with a rigidity substantially similar to that of polycarbonate.

4. The device according to claim 1 wherein said connecting means further comprises a flexible sleeve with an annular groove on an inner surface of said sleeve and said punch further comprises a cannula section and an integral base section said base section having an annular shoulder with dimensions slightly larger than said sleeve and equal to said annular ring, wherein said shoulder is engaged by said annular groove thereby securing said base in said sleeve.

5. The device according to claim 1 wherein said sleeve and said base are circular.

6. The device as disclosed in claim 1 wherein said fluid is blood or blood sera.

7. The device according to claim 1, wherein the plane of the distal end of said punch is formed at an oblique angle to the axis of said punch to sharpen the distal end and facilitate piercing of the punch through a rubber stopper.

* * * * *